(12) United States Patent
Rock et al.

(10) Patent No.: US 8,101,586 B2
(45) Date of Patent: Jan. 24, 2012

(54) METHODS AND COMPOSITIONS FOR THE TREATMENT OF STERILE INFLAMMATION

(75) Inventors: Kenneth L. Rock, Chestnut Hill, MA (US); Chun-Jen Chen, Taipei (TW)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 12/769,983

(22) Filed: Apr. 29, 2010

(65) Prior Publication Data

US 2010/0210711 A1 Aug. 19, 2010

Related U.S. Application Data

(62) Division of application No. 11/937,949, filed on Nov. 9, 2007, now Pat. No. 7,736,860.

(60) Provisional application No. 60/858,001, filed on Nov. 9, 2006.

(51) Int. Cl.
*A61K 48/00* (2006.01)

(52) U.S. Cl. .................................... 514/44 R

(58) Field of Classification Search ................. 514/44 R
See application file for complete search history.

(56) References Cited

U.S. PATENT DOCUMENTS

| | | | |
|---|---|---|---|
| 5,856,099 | A | 1/1999 | Miraglia et al. |
| 6,471,961 | B1 | 10/2002 | Tobinik |
| 6,989,244 | B1 | 1/2006 | Tsuchiya et al. |
| 7,033,830 | B2 | 4/2006 | Karras et al. |
| 7,115,402 | B2 | 10/2006 | Feder et al. |
| 2006/0179499 | A1* | 8/2006 | Tirabassi et al. ................. 800/14 |
| 2006/0276458 | A1 | 12/2006 | Chiou |

OTHER PUBLICATIONS

Hua et al. (Biochemical and Biophysical Research Communication 338 (2005), 1118-1125).*
Abraham, "Neutrophils and acute lung injury," *Crit. Care Med.*, 31:S195-S199 (2003).
Adachi et al., "Targeted disruption of the MyD88 gene results in loss of IL-1- and IL-18-mediated function," *Immunity*, 9:143-150 (1998).
Beck et al., "Generation of soluble interleukin-1 receptor from an immunoadhesin by specific cleavage," *Mol. Immunol.* 31(17):1335-1344 (1994).
Bless et al., "Protective effects of an aptamer inhibitor of neutrophil elastase in lung inflammatory injury," *Curr. Biol.*, 7:877-880 (1997).
Braddock and Quinn, "Targeting IL-1 in inflammatory disease: new opportunities for therapeutic intervention," *Nat. Rev.* 3:1-10 (2004).
Burch and Mahan, "Oligonucleotides antisense to the interleukin 1 receptor mRNA block the effects of interleukin 1 in cultured murine and human fibroblasts and in mice," *J. Clin. Invest.* 88(4):1190-1196 (1991).
Chen et al., "Neutrophil-derived leukotriene B4 is required for inflammatory arthritis," *J. Exp. Med.*, 203:837-842 (2006).

Dawson et al., "Effects of soluble interleukin-1 type II receptor on rabbit antigen-induced arthritis: clinical, biochemical and histological assessment," *Rheumatology*, 38(5):401-406 (1999).
Fadok et al., "Macrophages that have ingested apoptotic cells in vitro inhibit proinflammatory cytokine production through autocrine/paracrine mechanisms involving TGF-beta, PGE2, and PAF," *J. Clin. Invest.*, 101:890-898 (1998).
Fisher and Meiselmann, "Polymorphonuclear leukocytes in ischemic vascular disease," *Thromb. Res.*, 74(Suppl. 1):S21-S34 (1994).
Fredericks et al., "Identification of potent human anti-IL-1RI antagonist antibodies," *Protein Eng. Des. Sel.*, 17(1):95-106 (2004).
Hemmi et al., "A Toll-like receptor recognizes bacterial DNA," *Nature*, 408:740-745 (2000).
Hemmi et al., "Small anti-viral compounds activate immune cells via the TLR7 MyD88-dependent signaling pathway," *Nat. Immunol.*, 3:196-200 (2002).
Huynh et al., "Phosphatidylserine-dependent ingestion of apoptotic cells promotes TGF-beta1 secretion and the resolution of inflammation," *J. Clin. Invest.*, 109:41-50 (2002).
Jaeschke, "Mechanisms of Liver Injury. II. Mechanisms of neutrophil-induced liver cell injury during hepatic ischemia-reperfusion and other acute inflammatory conditions," *Am. J. Physiol. Gastrointest. Liver Physiol.*, 290:G1083-G1088 (2006).
Kim et al., "A unique requirement for the leukotriene B4 receptor BLT1 for neutrophil recruitment in inflammatory arthritis," *J. Exp. Med.*, 203:829-835 (2006).
Li et al., "An essential role of the NF-kappa B/Toll-like receptor pathway in induction of inflammatory and tissue-repair gene expression by necrotic cells," *J. Immunol.*, 166:7128-7135 (2001).
Liu et al., "Neutrophil depletion protects against murine acetaminophen hepatotoxicity," *Hepatology*, 43:1220-1230 (2006).
Majno et al., "Cellular death and necrosis: chemical, physical and morphologic changes in rat liver," *Virchows Arch. Pathol. Anat. Physiol. Klin. Med.*, 333:421-465 (1960).
Randle et al., "ICE/Caspase-1 inhibitors as novel anti-inflammatory drugs," *Exp. Op. Inv. Drugs*, 10(7):1207-1209 (2001).
Sadasivan et al., "Neutrophil mediated microvascular injury in acute, experimental compartment syndrome," *Clin. Orthop. Relat. Res.*, 206-2150 (1997).
Sawa et al., "Leukocyte depletion attenuates reperfusion injury in patients with left ventricular hypertrophy," *Circulation*, 93:1640-1646 (1996).
Scaffidi, "Release of chromatin protein HMGB1 by necrotic cells triggers inflammation," *Nature*, 418:191-195 (2002).
Sekido et al., "Prevention of lung reperfusion injury in rabbits by a monoclonal antibody against interleukin-8," *Nature*, 365:654-657 (1993).
Serhan et al., "Resolution of inflammation: the beginning programs the end," *Nat. Immunol.*, 6:1191-1197 (2005).
Shimizu et al., "Involvement of a NF-kappa B-like transcription factor in the activation of the interleukin-6 gene by inflammatory lymphokines," *Mol. Cell. Biol.*, 10(2):561-568 (1990).
Symons et al., "Purification and characterization of a novel soluble receptor for interleukin 1," *J. Exp. Med.*, 174(5):1251-1254 (1991).

(Continued)

*Primary Examiner* — Brian Whiteman
(74) *Attorney, Agent, or Firm* — Fish & Richardson P.C.

(57) ABSTRACT

Described are methods and compositions that inhibit IL-1 signalling for the treatment of acute inflammatory response to cell necrosis, and the attendant collateral tissue damage.

10 Claims, 10 Drawing Sheets

OTHER PUBLICATIONS

Symons et al., "Soluble type II interleukin 1 (IL-1) receptor binds and blocks processing of IL-1 beta precursor and loses affinity for IL-1 receptor antagonist," *Proc. Natl. Acad. Sci. U. S. A.*, 92(5):1714-1718 (1995).

Takeuchi et al., "Cutting edge: role of Toll-like receptor 1 in mediating immune response to microbial lipoproteins," *J. Immunol.*, 169:10-14 (2002).

Takeuchi et al., "Differential roles of TLR2 and TLR4 in recognition of gram-negative and gram-positive bacterial cell wall components," *Immunity*, 11:443-451 (1999).

Takeuchi et al., "Discrimination of bacterial lipoproteins by Toll-like receptor 6," *Int. Immunol.*, 13:933-940 (2001).

Valentino et al., "First clinical trial of a novel caspase inhibitor: anti-apoptotic caspase inhibitor, IDN-6556, improves liver enzymes," *Int. J. Clin. Pharmacol. Ther.*, 41(10):441-449 (2003).

Vickers et al., "Modification of MyD88 mRNA splicing and inhibition of IL-1beta signaling in cell culture and in mice with a 2'-O-methoxyethyl-modified oligonucleotide," *J. Immunol.*, 176(6):3652-3661 (2006).

Watson et al., "The IL-1☐-converting enzyme (caspase-1) inhibits apoptosis of inflammatory neutrophils through activation of IL-1☐," *J. Immunol.*, 161:957-1962 (1998).

Wipke et al., "Essential role of neutrophils in the initiation and progression of a murine model of rheumatoid arthritis," *J. Immunol.*, 167:1601-1608 (2001).

Yamamoto et al, "Role of adaptor TRIF in the MyD88-independent toll-like receptor signaling pathway," *Science*, 301:640-643 (2003).

Yamamoto et al, "TRAM is specifically involved in the Toll-like receptor 4-mediated MyD88-independent signaling pathway," *Nat. Immunol.*, 4:1144-1150 (2003).

Yamamoto et al., "Essential role for TIRAP in activation of the signalling cascade shared by TLR2 and TLR4," *Nature*, 420:324-329 (2002).

Zhang et al., "A toll-like receptor that prevents infection by uropathogenic bacteria," *Science*, 303:1522-1526 (2004).

Zingarelli et al., "Blockade of Poly(ADP-ribose) synthetase inhibits neutrophil recruitment, oxidant generation, and mucosal injury in murine colitis," *Gastroenterology*, 116:335-345 (1999).

Fitzgerald et al., "LPS-TLR4 Signaling to IRF-3/7 and NF-κB Involves the Toll Adapters TRAM and TRIF," *J. Exp. Med.* 198:1043-1055, 2003.

Jordan et al., "The Role of Neutrophils in Myocardial Ischemia—Reperfusion Injury," *Cardiovascular Res.* 43:860-878, 1999.

Rubin and Farber, Pathology, Third Edition, Lippincott Raven, 1998, pp. 556-561.

\* cited by examiner

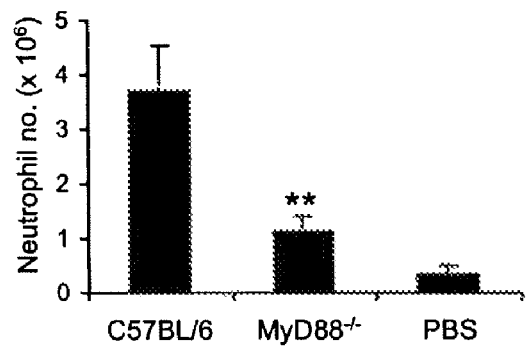
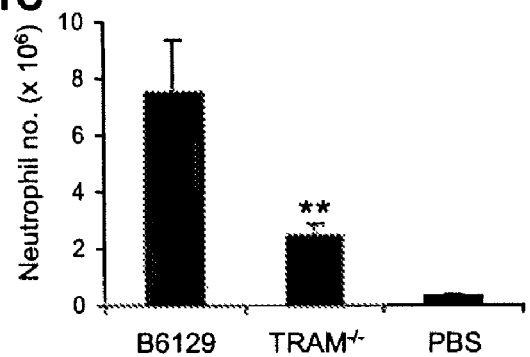
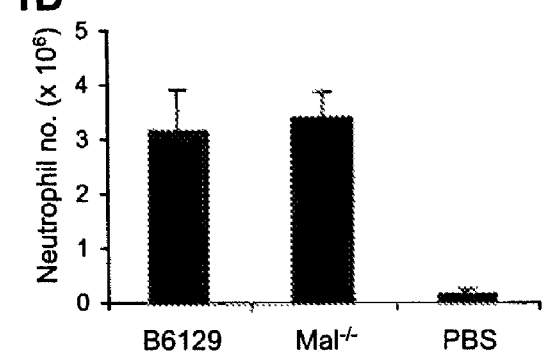
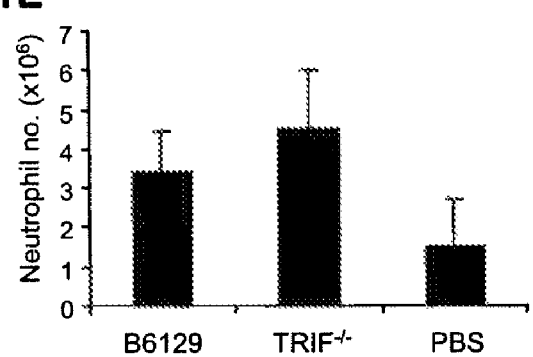
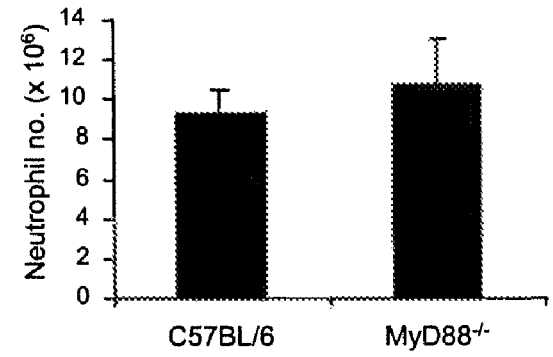
Figures 1B-F

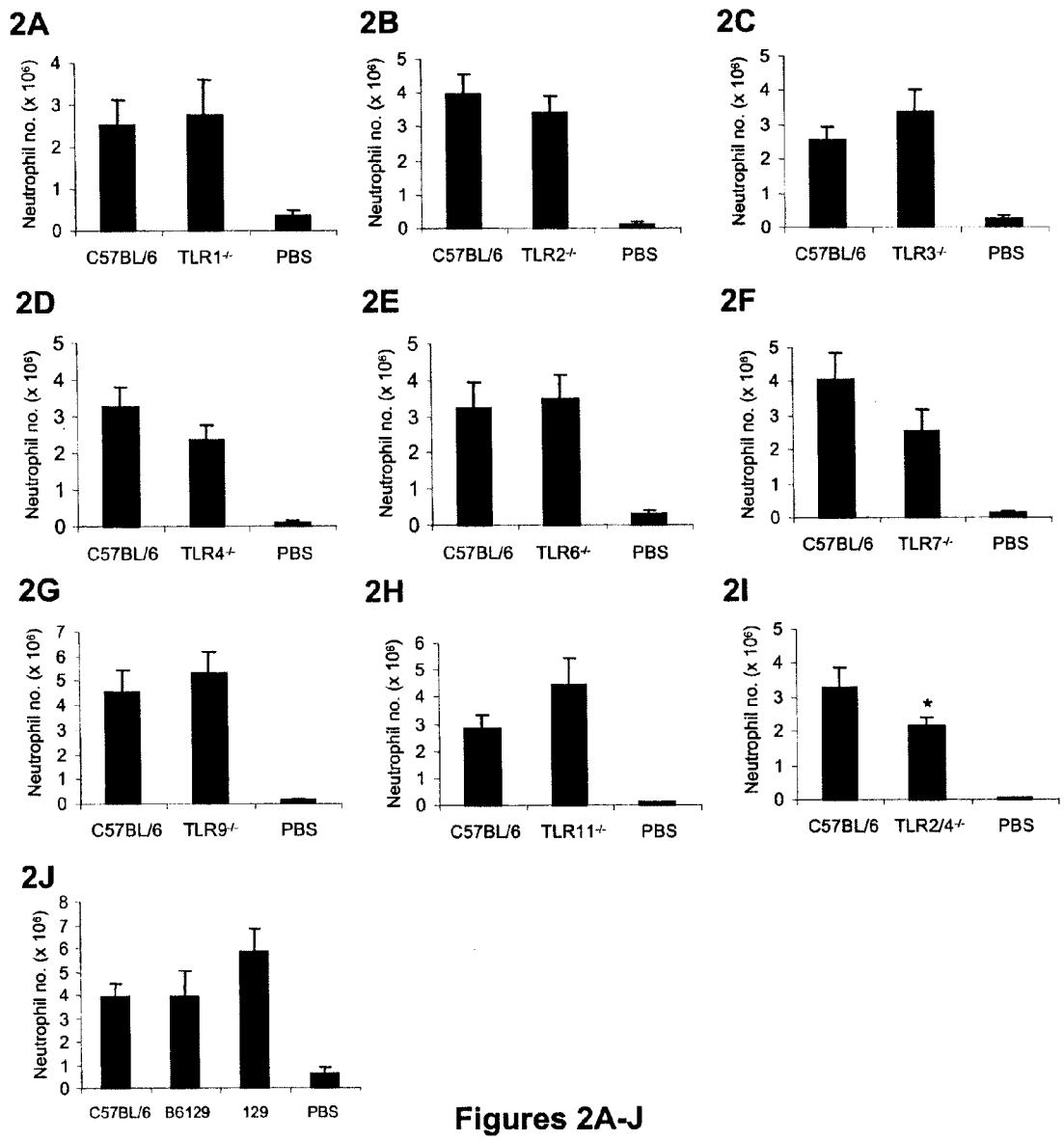
Figures 2A-J

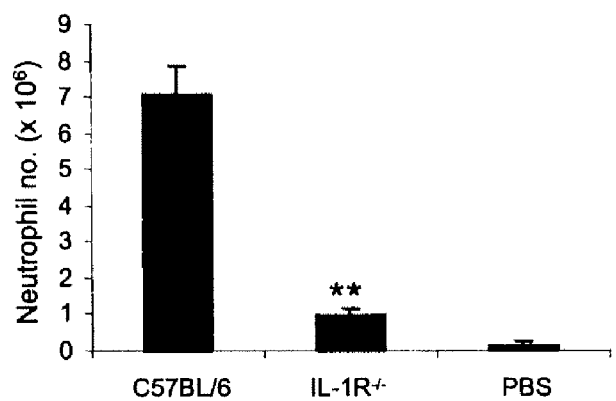
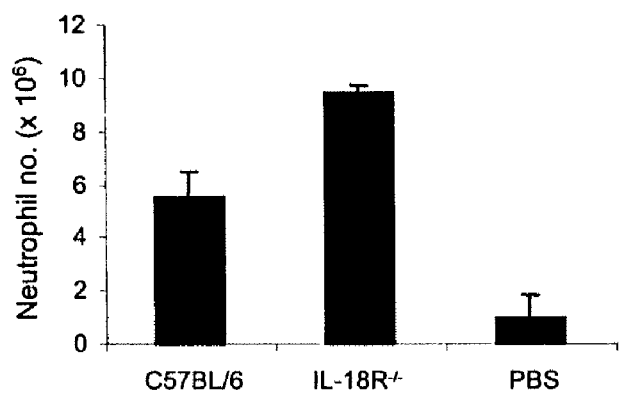
Figures 3A-B

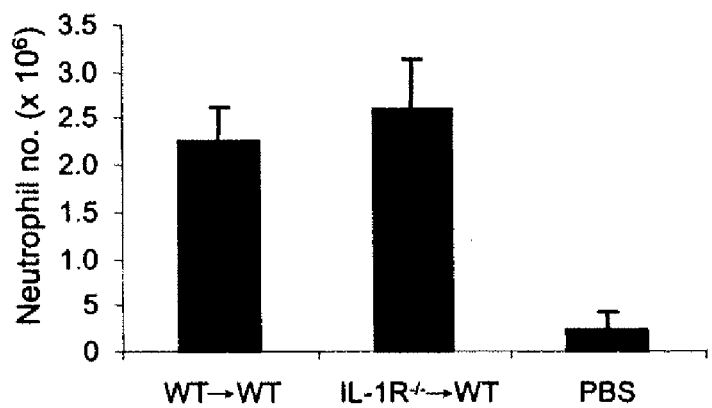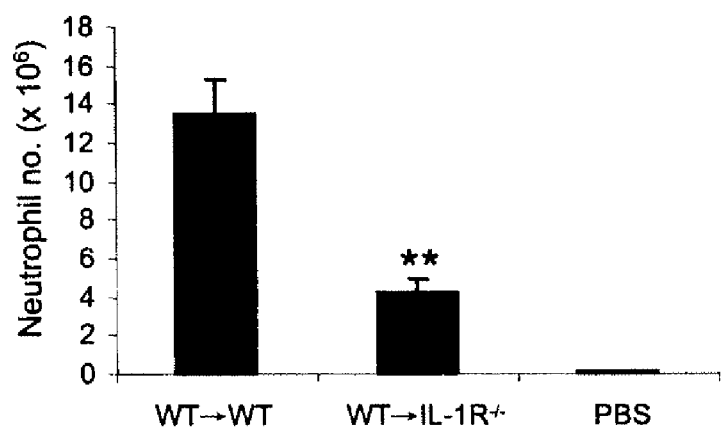
Figures 4A-B

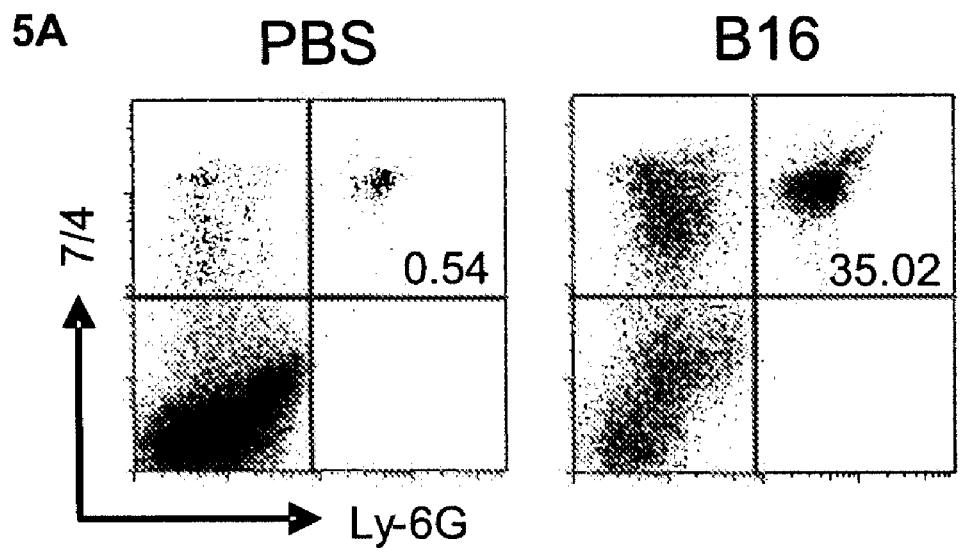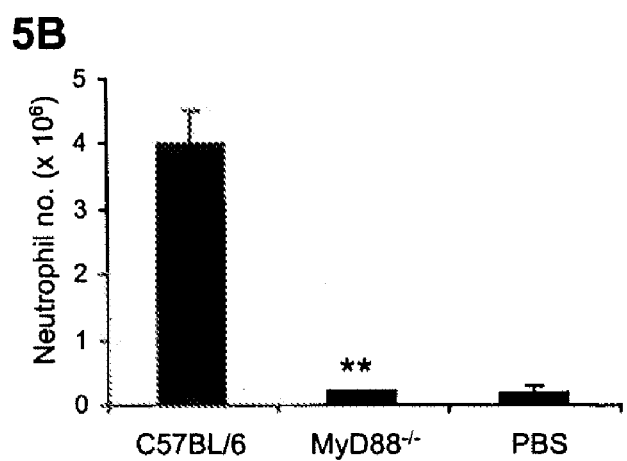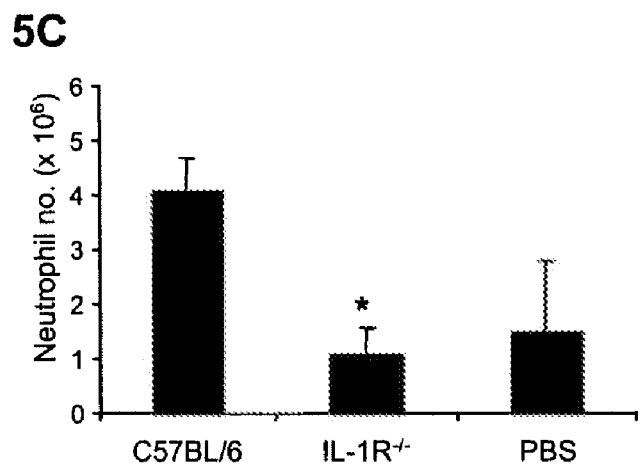
Figures 5A-C

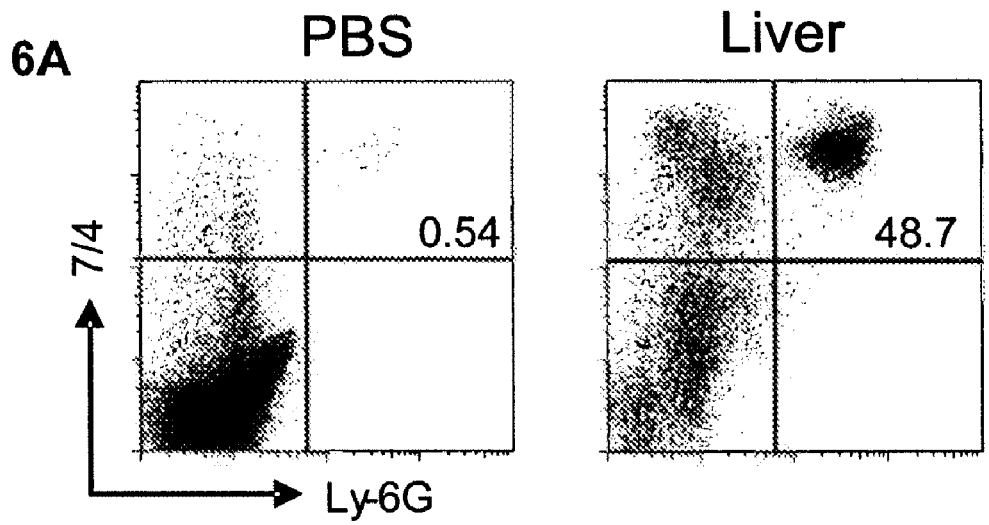
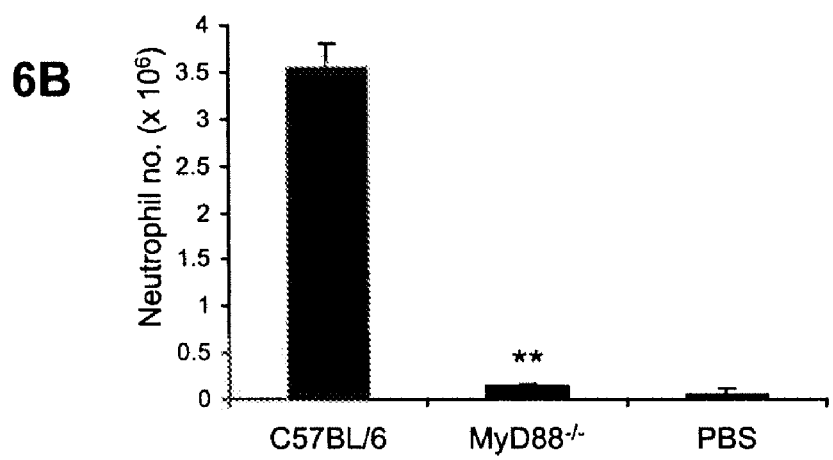
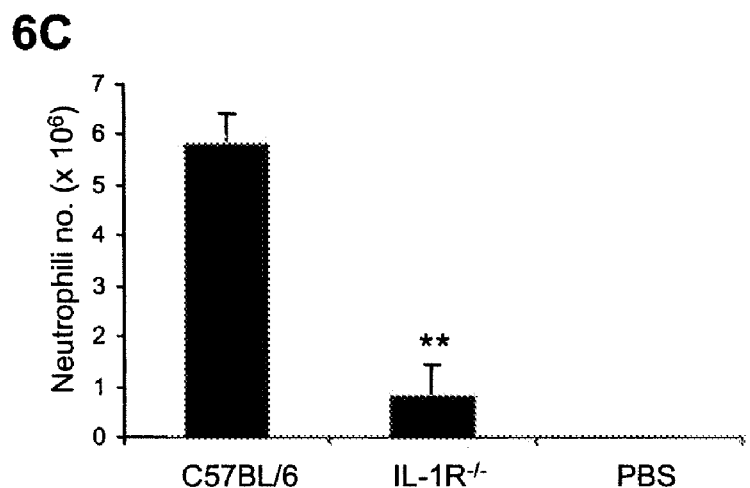
Figures 6A-C

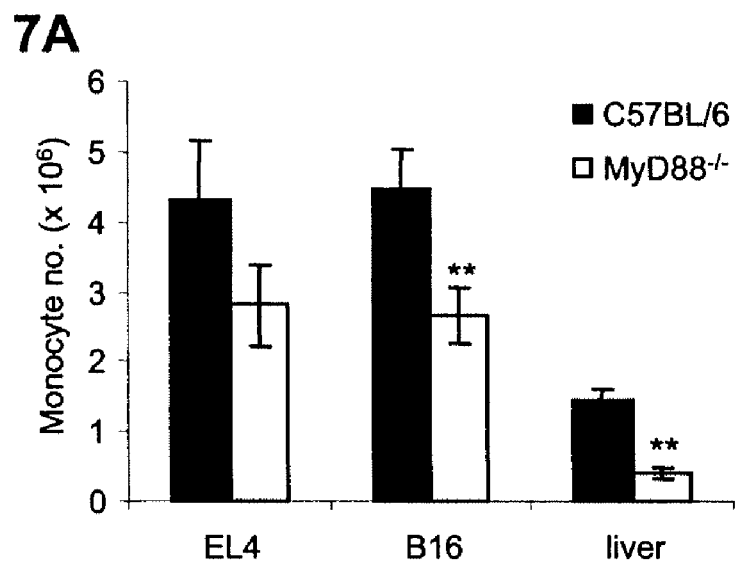
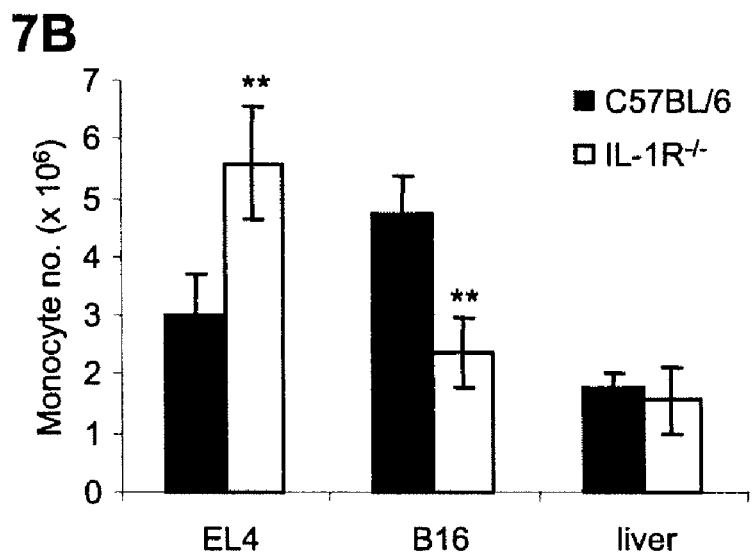
Figures 7A-B

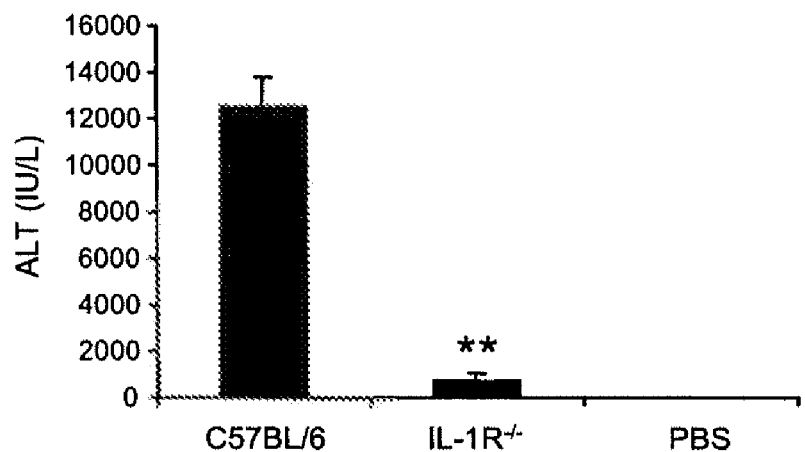
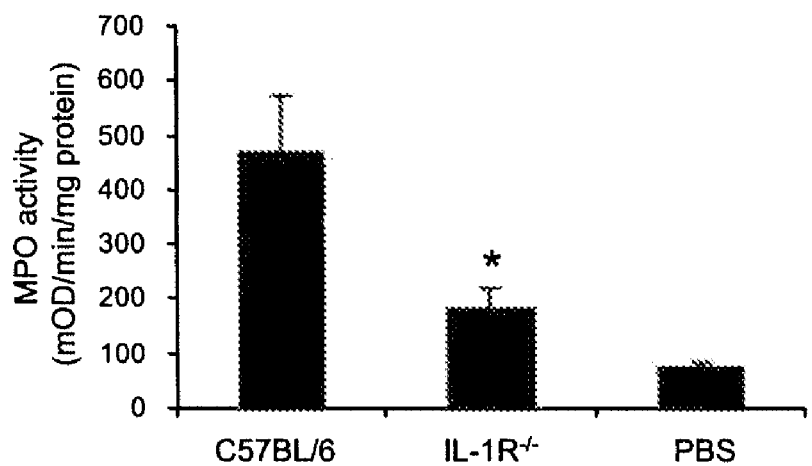
Figures 8A-B

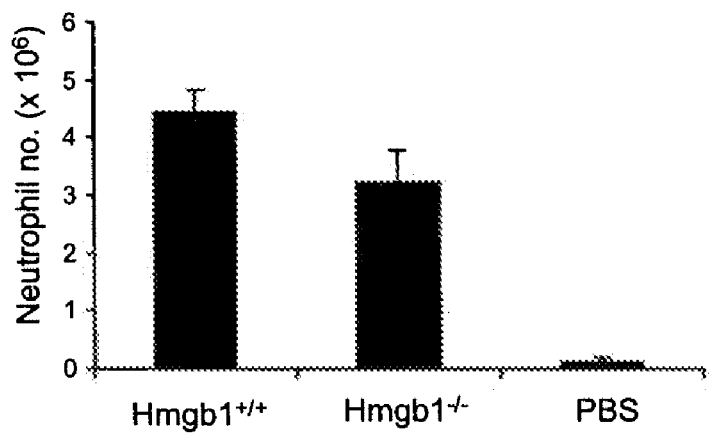
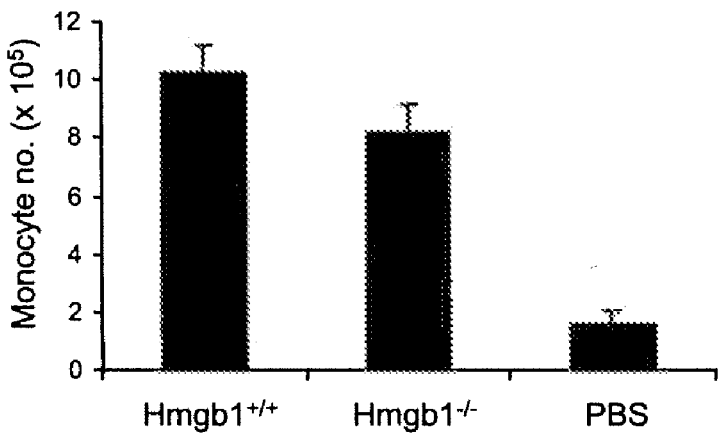
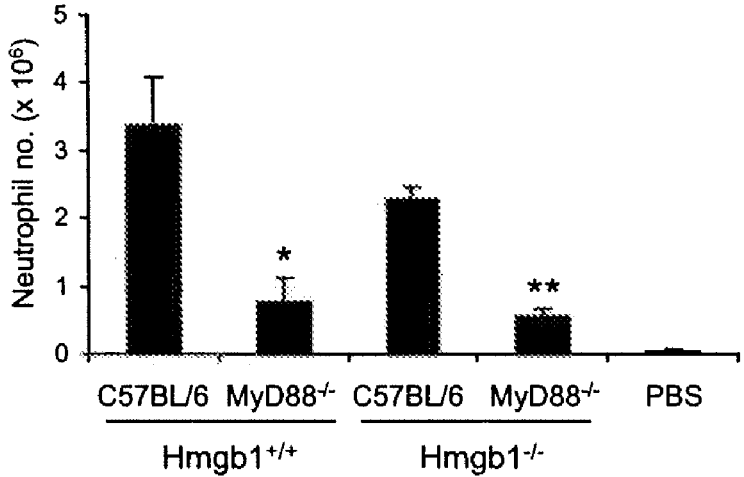
Figures 9A-C

METHODS AND COMPOSITIONS FOR THE TREATMENT OF STERILE INFLAMMATION

CLAIM OF PRIORITY

This divisional application claims the benefit of U.S. patent application Ser. No. 11/937,949, filed Nov. 9, 2007, now U.S. Pat. No. 7,736,860, which claims the benefit of U.S. Patent Application Ser. No. 60/858,001, filed on Nov. 9, 2006, the entire contents of which are hereby incorporated by reference.

FEDERALLY SPONSORED RESEARCH OR DEVELOPMENT

This invention was made with Government support under Grant No. PO1 AI-057784-03 awarded by the National Institutes of Health. The Government has certain rights in the invention.

TECHNICAL FIELD

This invention relates to methods of treating sterile inflammation.

BACKGROUND

In vivo, necrotic cell death almost inevitably provokes an inflammatory response (Majno et al., "Cellular death and necrosis: chemical, physical and morphologic changes in rat liver," Virchows Arch. Pathol. Anat. Physiol. Klin. Med., 333:421-465, 1960). Within minutes, there is an influx of neutrophils and at later times monocytes into injured tissues. This response is elicited by most types of injured cells and is so stereotypical that it is used to help identify cell death in vivo and even estimate the time at which it occurred, e.g., after an ischemic insult such as a myocardial infarction (Antman, Acute myocardial infarction. In Heart Disease: A Textbook of Cardiovascular Medicine, 6th ed. B. E., Z. D. P., and L. P., editors. Philadelphia, Pa.: WB Saunders. 1114-1231, 2001). This sterile inflammatory response to injured cells is medically important. Acutely, it can cause pain, dysfunction and further tissue damage that may actually do more harm than good, in at least some settings. Chronically, the sterile inflammation provoked by ongoing tissue damage is thought to contribute to the pathogenesis of many diseases, including ischemia-induced injuries (Fisher and Meiselmann, "Polymorphonuclear leukocytes in ischemic vascular disease," Thromb. Res., 74 Suppl. 1:S21-34, 1994), rheumatoid arthritis (Wipke and Allen, "Essential role of neutrophils in the initiation and progression of a murine model of rheumatoid arthritis," J. Immunol. 167:1601-1608, 2001; Chen et al., "Neutrophil-derived leukotriene B4 is required for inflammatory arthritis," J. Exp. Med. 203:837-842, 2006; Kim et al., "A unique requirement for the leukotriene B4 receptor BLT1 for neutrophil recruitment in inflammatory arthritis," J. Exp. Med., 203:829-835, 2006), acute lung injury (Abraham, "Neutrophils and acute lung injury," Crit. Care Med. 31:S195-199, 2003), drug-induced liver injury (Liu et al., "Neutrophil depletion protects against murine acetaminophen hepatotoxicity," Hepatology 43:1220-1230, 2006), inflammatory bowel diseases (Zingarelli et al., "Blockade of Poly(ADP-ribose) synthetase inhibits neutrophil recruitment, oxidant generation, and mucosal injury in murine colitis," Gastroenterology, 116:335-345, 1999). It is therefore important to elucidate the mechanisms underlying the sterile inflammatory response to injured cells. Ultimately, these mechanisms might be important targets of pharmacological intervention.

The inflammatory response to dying tissues is thought to serve several functions. Cell death may help to alert the immune system to potential danger such as an infection. The ensuing inflammatory response rapidly mobilizes leukocytes that attempt to contain and/or eliminate an infection, if present. Even if an infection isn't present, the recruited leukocytes play an important role in removing the dead cells and stimulating tissue repair mechanisms (Serhan and Savill, "Resolution of inflammation: the beginning programs the end," Nat. Immunol., 6:1191-1197, 2005; Fadok et al., "Macrophages that have ingested apoptotic cells in vitro inhibit proinflammatory cytokine production through autocrine/paracrine mechanisms involving TGF-beta, PGE2, and PAF," J. Clin. Invest., 101:890-898, 1998; Huynh et al., "Phosphatidylserine-dependent ingestion of apoptotic cells promotes TGF-beta1 secretion and the resolution of inflammation," J. Clin. Invest., 109:41-50, 2002). While these aspects of the inflammatory response are beneficial, the recruited leukocytes can also damage healthy cells. In the absence of infection, this "sterile inflammation" may cause dysfunction and disease (Sadasivan et al., "Neutrophil mediated microvascular injury in acute, experimental compartment syndrome," Clin. Orthop. Relat. Res., 206-215, 1997; Bless et al., "Protective effects of an aptamer inhibitor of neutrophil elastase in lung inflammatory injury," Curr. Biol. 7:877-880, 1997; Sawa et al., "Leukocyte depletion attenuates reperfusion injury in patients with left ventricular hypertrophy," Circulation, 93:1640-1646, 1996; Sekido et al., "Prevention of lung reperfusion injury in rabbits by a monoclonal antibody against interleukin-8," Nature, 365:654-657, 1993; Jaeschke, "Mechanisms of Liver Injury. II. Mechanisms of neutrophil-induced liver cell injury during hepatic ischemia-reperfusion and other acute inflammatory conditions," Am. J. Physiol. Gastrointest. Liver Physiol., 290:G1083-1088, 2006). It is therefore important to understand the basis of the sterile inflammatory response to tissue injury.

SUMMARY

To stimulate an inflammatory response, dying cells must express or release proinflammatory molecules. The identity of these factors and how they are sensed is poorly understood.

In infections and autoimmunity, triggers of inflammation stimulate the elaboration of proinflammatory mediators that actually initiate and amplify the inflammatory response. This same mechanism presumably operates in sterile inflammatory responses. Complement activation was suggested to be a mechanism for the pathogenesis of necrotic tissue-induced inflammation (Li et al., "An essential role of the NF-kappa B/Toll-like receptor pathway in induction of inflammatory and tissue-repair gene expression by necrotic cells," J. Immunol., 166:7128-7135, 2001). However, the major downstream mediators that drive the inflammatory response to tissue injury have not been clearly defined.

The present invention is based, at least in part, on the discovery that IL-1R expression and its signaling through Myeloid Differentiation Primary Response Gene 88 (MyD88) on parenchymal cells play pivotal roles in mediating the sterile inflammatory response. The results described herein demonstrate that this is a major pathway that is essential for the neutrophil response to tissue injury, and is therefore a suitable target for therapeutic and prophylactic intervention. While IL-1 was generally suspected to be one of many mediators generated in settings of inflammation, the key and dominant role of this cytokine in driving the sterile inflammatory response to dying cells was not known. Thus it was not previously known what mediators were the essential targets to control therapeutically and it was not practical to attempt to target simultaneously all of the mediators produced. The discovery described herein is of the central role that this one cytokine, IL-1, plays in generating the sterile inflammatory response, and that blocking the actions of IL-1 is effective in blocking sterile inflammation to cell death and its attendant tissue damage.

Thus, the methods include blocking IL-1 production, IL-1 itself, IL-1R and/or the IL-1R signaling pathway to reduce the acute inflammatory response to cell injury and death, and the attendant collateral tissue damage. The methods can be used in conditions associated with cell necrosis that provokes sterile inflammation. Such conditions can include trauma and wounds (including surgical wounds); acute respiratory distress syndrome (diffuse alveolar damage) and other lung diseases with necrosis-associated inflammation; asthma; necrotic glomerulonephritis; necrotic vasculitis; necrotic pancreatitis; inflammatory bowel disease; necrotic damage from toxic agents or drugs; and necrotic hepatitis. In some embodiments, the condition is associated with an ischemic injury resulting in necrosis.

In a first aspect, the invention provides methods for treating, preventing, or delaying development or progression of a condition associated with sterile inflammation caused by necrosis in a subject. The methods include administering to the subject a therapeutically effective amount of a compound that inhibits IL-1 signalling. In some embodiments, the methods include detecting the presence of necrotic cells or tissues in a subject who has, or is at risk of having, a condition associated with sterile inflammation; and selecting the subject if necrotic cells are present.

Compounds that inhibit IL-1 signalling are described herein, e.g., inhibitors of IL-1 production; inhibitory nucleic acids that decrease expression of IL-1 pathway molecules (e.g., IL-1, IL-1R, MyD88, TRAF6, TAK1, NIK/MKK, IKK, NF-kappaB, or caspase); naturally occurring inhibitors of IL-1 signalling, e.g., IL-1 receptor antagonist (IL-1 RA) and IL-1 receptor type II (IL-1 R type II); and ICE/caspase inhibitors.

In some embodiments, the condition associated with sterile inflammation caused by necrosis is sterile inflammation associated with pancreatitis.

In some embodiments, the condition associated with sterile inflammation caused by necrosis is sterile inflammation associated with ischemic injury, e.g., an injury to cardiac tissue, uterine tissue, renal tissue, hepatic tissue, neural tissue, muscle tissue, dermal tissue, or other organ. The ischemic injury can be caused by, e.g., a surgical intervention, e.g., an organ transplantation procedure; for example, the necrosis can be in a transplanted organ.

In some embodiments, administration of the inhibitor is by local administration to the necrotic cells or a tissue or organ comprising the necrotic cells.

In a further aspect, the invention includes methods for identifying candidate compounds useful in the treatment, prevention, or delay of development or progression of a condition associated with sterile inflammation. The methods include providing a sample comprising one or more of MyD88, IL-1, or IL-1 receptor; contacting the sample with one or more test compounds; and detecting binding of a test compound to the MyD88, IL-1, or IL-1 receptor in the sample. A test compound that binds to the MyD88, IL-1, or IL-1 receptor in the sample is a candidate compound useful in the treatment, prevention, or delay of development or progression of a condition associated with sterile inflammation.

In some embodiments, the methods also include selecting a test compound that binds to the MyD88, IL-1, or IL-1 receptor; providing a cell comprising functional MyD88, IL-1 and IL-1 receptor; contacting the cell with the test compound; assaying an effect of the test compound on the MyD88/IL-1 signalling in the cell. A test compound that inhibits MyD88/IL-1 signalling in the cell is a candidate compound useful in the treatment, prevention, or delay of development or progression of a condition associated with sterile inflammation.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1B-1F are bar graphs illustrating neutrophil numbers determined by multiplying the total cell numbers with the percentage of Ly-6G$^+$, 7/4$^+$ cells (n=3) in C57BL/6 mice as compared to mice deficient for MyD88 (1B), B6129 mice as compared to mice deficient for TRAM (1C), B6129 mice as compared to mice deficient for Mal (1D), or B6129 mice as compared to mice deficient for TRIF (1E) after challenge i.p. with necrotic EL4 cells as described herein. At 16 hours after challenge, PEC were stained for Ly-6G and 7/4 expression and analyzed by flow cytometry.

FIG. 1F is a bar graph showing neutrophil numbers in C57BL/6 or MyD88$^{-/-}$ mice challenged with 0.5 mg zymosan; PEC were analyzed for neutrophil numbers at 4 hours. Means and standard errors in FIGS. 1B-F are combined data from two or more independent experiments, and n's reported are the number of animals combining multiple experiments for each group. **, P<0.01 versus controls (C57BL/6 in 1B; B6129 in 1C-E).

FIGS. 2A-J are bar graphs illustrating neutrophil numbers in C57BL/6 mice and mice deficient for (2A) Toll-like receptor 1 (TLR1), (2B) TLR2, (2C) TLR3, (2D) TLR4, (2E) TLR6, (2F) TLR7, (2G) TLR9, (2H) TLR11, or (2I) TLR2/4, 16 hours after i.p. challenge with necrotic EL4 cells. C57BL/6 mice challenged with PBS served as negative controls. Means and standard errors shown are combined data from two or more independent experiments, and n's reported are the number of animals combining multiple experiments for each group. *, P<0.05 versus control (C57BL/6).

FIGS. 3A-B are bar graphs illustrating neutrophil numbers in C57BL/6 mice and mice deficient for (3A) IL-1R or (3B) IL-18R challenged i.p. with necrotic EL4 cells as described in the METHODS. C57BL/6 mice challenged with PBS served as negative controls. At 16 hours after challenge, neutrophil numbers in the PEC were determined (n=3 in 3A, and n=4 in 3B). Data shown are representative of three independent experiments. **, P<0.01 versus control (C57BL/6).

FIGS. 4A-B are bar graphs illustrating neutrophil numbers 16 hours after i.p. challenge with necrotic EL4 cells (in PBS) in bone marrow chimeras generated as described herein. 4A, C57BL/6 (WT) mice served as hosts, and B6.SJL (WT) or IL-1R$^{-/-}$ mice served as bone marrow donors. 4B, C57BL/6 (WT) and IL-1R$^{-/-}$ mice served as hosts, and B6.SJL (WT) mice served as bone marrow donors. C57BL/6 mice challenged with PBS served as negative controls. Data shown are representative of four independent experiments. **, P<0.01 versus control (WT→WT).

FIG. 5A is a representative dot plot of Ly-6G and 7/4 expression on PEC in C57BL/6 mice injected 16 hours earlier with PBS or necrotic B16 cells.

FIGS. 5B-C are bar graphs illustrating neutrophil numbers in C57BL/6 mice and mice deficient for MyD88 (5B) or IL-1R (5C), 16 hours after i.p. challenge with necrotic B16 cells as described herein. C57BL/6 mice challenged with PBS served as negative controls. (n=3 in B; n=4 for C57BL/6 and n=2 for IL-1$^{-/-}$ in C). *, P<0.05; **, P<0.01 versus control (C57BL/6).

FIG. 6A is a representative dot plot of Ly-6G and 7/4 expression on PEC in C57BL/6 mice injected 16 hours earlier with PBS or liver homogenate.

FIGS. 6B-C are bar graphs illustrating neutrophil numbers in C57BL/6 mice and mice deficient for MyD88 (6B) or IL-1R (6C) 16 hours after i.p. challenge with liver homogenate as described in the METHODS. C57BL/6 mice challenged with PBS served as negative controls. (n=4 in B and n=5 in C). **, P<0.01 versus control (C57BL/6).

FIGS. 7A-B are bar graphs illustrating monocyte numbers in C57BL/6 mice and mice deficient for MyD88 (7A) or IL-1R (7B), 16 hours after i.p. challenge with necrotic EL4, B16, or liver homogenate as indicated. Monocyte numbers in the PEC were determined by multiplying the total cell numbers with the percentage of Ly-6G$^-$, 7/4$^+$ cells. Means and standard errors shown are combined data from two or more independent experiments, and n's reported are the number of animals combining multiple experiments for each group. **, P<0.01 versus control (C57BL/6).

FIGS. 8A-B are bar graphs illustrating serum ALT activities (8A) and liver tissue myeloperoxidase activity (8B) in C57BL/6 mice and mice deficient for IL-1 18 hours after challenge with 300 mg/kg acetaminophen as described herein. C57BL/6 mice challenged with PBS served as negative controls (n=6). Data shown are representative of three experiments. *, P<0.05; **, P<0.01 versus control (C57BL/6).

FIGS. 9A-B are bar graphs illustrating neutrophil and monocyte numbers in Hmgb1$^{+/+}$ and Hmgb1$^{-/-}$ cells that were UV-irradiated and injected i.p. into C57BL/6 mice as described herein. C57BL/6 mice challenged with PBS served as negative controls. At 16 hours after challenge, neutrophil (9A) and monocyte (9B) numbers in the PEC were determined. Means and standard errors shown are combined data from two independent experiments, and n's reported are the number of animals combining two experiments for each group.

FIG. 9C is a bar graph illustrating neutrophil numbers in C57BL/6 and MyD88$^{-/-}$ mice were challenged i.p. with necrotic Hmgb1$^{+/+}$ or Hmgb1$^{-/-}$ cells. At 16 hours after challenge, neutrophil numbers in the PEC were determined (n=4). Data shown are representative of three experiments. *, P<0.05; **, P<0.01 versus control (C57BL/6).

DETAILED DESCRIPTION

Figure 1A:
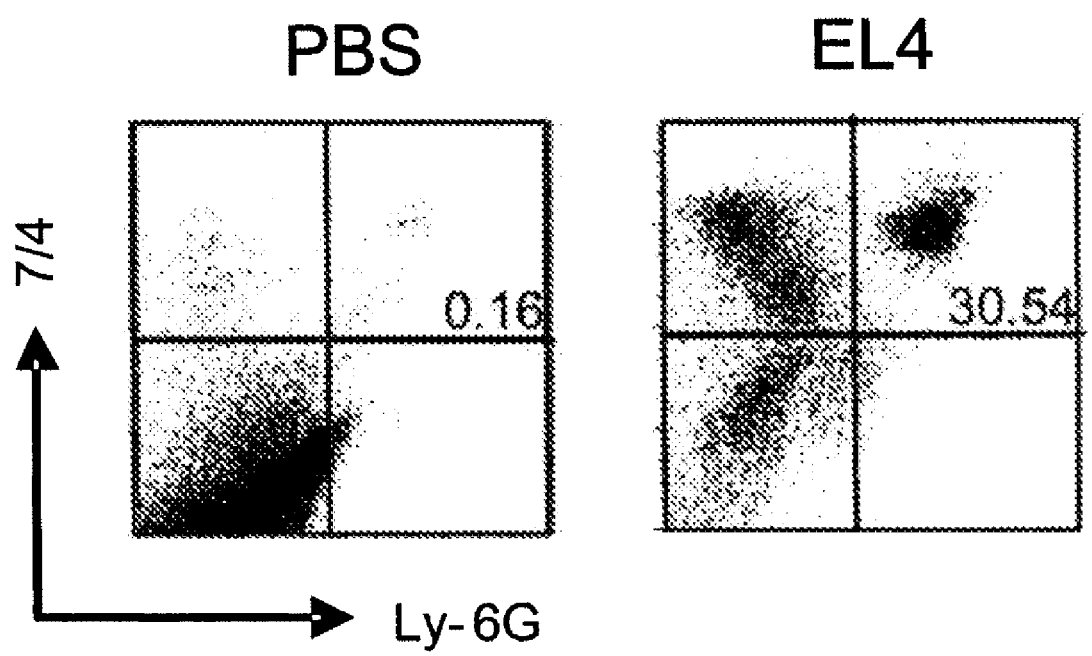
FIG. 1A is a representative dot plot of FACS analysis of Ly-6G and 7/4 expression on peritoneal exudate cells (PECs) in C57BL/6 mice injected 16 hours earlier with PBS or necrotic EL4 cells.

As noted above, necrotic cell death almost inevitably provokes an inflammatory response, referred to as "sterile inflammation" in the absence of infection. Once dead cells are sensed, the subsequent downstream pathways that stimulate sterile inflammation are poorly understood. As described herein, the Toll/IL-1 receptor (TIR) adaptor protein MyD88 plays a major role in the acute inflammatory response to dead cells. Since the reduction in inflammation was profound in MyD88-deficient mice but not in TLR-deficient mice, the other known MyD88-dependent receptors, IL-1R and IL18R, were also studied. IL-1R-deficient mice showed a similar reduction in inflammation as MyD88-negative mice while the response of IL-18R mutant mice was normal. Therefore, IL-1R signaling is a central mediator in the sterile inflammatory response.

Blocking sterile inflammation is an attractive strategy to limit the damage of acute inflammation and to stop the ongoing damage in chronic inflammation to tissue injury. Therefore, as described herein, agents that block IL-1 are expected to be useful in limiting tissue damage during sterile inflammation. In support of this concept, hepatocyte damage (assayed by ALT release) induced by a toxic insult (acetaminophen) is reduced in IL-1R-deficient mice, as shown herein.

Therapeutic and Prophylactic Interventions

The methods described herein include methods for treating and preventing the progression or onset of tissue damage associated with sterile inflammation in response to cell death. Sterile inflammation, as used herein, is a condition where neutrophils and other leukocytes infiltrate into the extracellular space of tissues n the absence of any infection. Thus, the methods described herein can be used to treat subjects who have sterile inflammation associated with cell necrosis, or to prevent the development of sterile inflammation in subjects who have cell necrosis and who have or are at high risk of developing sterile inflammation, e.g., subjects who have had an ischemic injury or other sterile trauma.

Thus, the methods described herein can include detecting the presence of cell necrosis in a subject, i.e., in a tissue of the subject, and selecting a subject on the basis that they have cell necrosis, and administering to the subject an effective amount of a composition described herein, e.g., a composition that inhibits IL-1 signalling, as defined herein.

A potential problem with potently blocking the inflammatory response is that this can decrease the ability of the host to prevent or contain infections and might interfere with tissue repair. In this context, it is interesting that MyD88-deficient animals still mount an acute inflammatory response, particularly neutrophil recruitment, to a microbial stimulus, zymosan. This finding indicates that IL-1 pathway blockade might have less of an effect on inflammation to microbes than on sterile inflammation.

Moreover, although MyD88 and IL-1R-deficient animals show a marked reduction in the neutrophil response, the recruitment of monocytes was not affected or even much diminished. Thus, blocking the IL-1 pathway therapeutically is expected to limit the damaging effects of neutrophils while retaining host defense and tissue repair functions of monocytes. This indicates that IL-1 pathway blockade is expected to have therapeutic benefit in sterile inflammation without markedly increasing susceptibility to infection or compromising healing.

Thus, the invention also includes methods for the administration and use of therapeutic compounds described herein in the treatment, prevention, or delay of development or progression of a condition associated with sterile inflammation caused by cell necrosis.

Detection of Cell Necrosis

A number of methods are known in the art for detecting cell necrosis. For example, a biopsy sample can be taken of the tissue suspected of including necrotic cells, and necrosis can be detected in the sample using standard methods, e.g., using detection of biochemical markers of necrosis, immunohistochemical markers of necrosis, or morphological markers of necrosis. The intact membrane of living cells excludes cationic dyes, such as propidium iodide (PI), 7-Amino-actinomycin D (7-AAD), or trypan blue. Due to the extensive membrane damage associated with necrosis, necrotic cells can be stained by short incubations with these agents, e.g., PI. Apoptotic cells (with the exception of cells in the late stages of apoptosis, which behave more like necrotic cells in these assays) show an uptake of PI that is much lower than that of necrotic cells. Thus, PI staining can be used distinguish healthy cells (PI negative), apoptotic cells (PI dim) and necrotic (PI bright) cells from each other. Thus, methods that detect uptake of molecules such as propidium iodide (PI, e.g., Calbiochem, CA) or 7-Amino-actinomycin D (7-AAD, e.g., Calbiochem, CA), which indicate the loss of plasma membrane integrity associated with necrosis, can be used.

Flow cytometry is one useful way to detect necrotic cells. For example, a flow cytometer with forward (FSC) and side) (90° scatter (SSC) detection can be used. A cell passing through the laser beam in a flow cytometer generates light scatter, and FSC provides information about cell size, while SSC provides information about the morphological complexity. Cell death is associated with changes in both morphology and size, which change light scatter in flow cytometry. In particular, when a cell dies by necrosis, both FSC and SSC tend to increase, probably as a consequence of cell swelling. Then FSC and SSC rapidly decrease, probably as a consequence of plasma membrane damage and leakage of cell constituents.

Alternatively, methods that detect necrosis in vivo can be used. For example, methods are known in the art for using magnetic resonance imaging (MRI) (see, e.g., Gabriel et al., "MRI detection of uterine necrosis after uterine artery embolization for fibroids," Am. J. Roentgenology 183(3):733-736, 2004); Positano et al., "A fast and effective method to assess myocardial necrosis by means of contrast magnetic resonance imaging," J. Cardiovasc. Magn. Reson. 7(2):487-94, 2005) or myocardial scintigraphy (Willerson, "Technetium 99 m stannous pyrophosphate myocardial scintigraphy to detect myocardial necrosis," West. J. Med., 127(6):510-512, 1977) to detect necrosis.

Inhibitors of IL-1 Signalling

As used herein, inhibitors of IL-1 signalling act directly on molecules of the IL-1 signalling pathway: IL-1, IL-1R, MyD88, TRAF6, TAK1, NIK/MKK, IKK, NF-kappaB, or caspase. Interleukin-1 (IL-1) is a proinflammatory cytokine which has been implicated in the inflammatory response occurring in the brain, spinal cord, retina, muscle, and elsewhere in the body; inhibitors useful in the present invention reduce the biologic effect of IL-1. In some embodiments, the inhibitor of IL-1 signalling acts directly on IL-1 or the IL-1R, i.e., binds to IL-1 or IL-1R proteins or nucleic acids encoding IL-1 or IL-R.

Inhibitors of IL-1 signalling can take several forms. For examples, inhibitors of IL-1 signalling can be cytokine neutralizing agents. They may be antibodies, e.g., monoclonal antibodies or antigen binding fragments. They may take the form of a soluble receptor to IL-1, e.g., as described in Beck et al., "Generation of soluble interleukin-1 receptor from an immunoadhesin by specific cleavage," Mol. Immunol. 31(17):1335-44, 1994). Soluble receptors freely circulate in the body. When they encounter their target cytokine (i.e., IL-1) they bind to it, effectively inactivating the cytokine, since the cytokine is then no longer able to bind with its biologic target in the body. An even more potent antagonist consists of two soluble receptors fused together, e.g., to a specific portion of an immunoglobulin molecule (Fc fragment). This produces a dimer composed of two soluble receptors which have a high affinity for the target, and a prolonged half-life.

There are two naturally occurring inhibitors of IL-1 signalling: IL-1 receptor antagonist (IL-1 RA) and IL-1 receptor type II (IL-1 R type II); see, e.g., Symons et al., "Purification and characterization of a novel soluble receptor for interleukin 1," J. Exp. Med., 174(5):1251-4, 1991); and Symons et al., "Soluble type II interleukin 1 (IL-1) receptor binds and blocks processing of IL-1 beta precursor and loses affinity for IL-1 receptor antagonist," Proc. Natl. Acad. Sci. U.S.A., 92(5):1714-8, 1995). IL-1RA is approved in the U.S. for the treatment of rheumatoid arthritis, under the trade name ANKINRA. Soluble IL-1R II is also in clinical trials for the treatment of RA, and has demonstrated efficacy pre-clinically (Dawson et al., "Effects of soluble interleukin-1 type II receptor on rabbit antigen-induced arthritis: clinical, biochemical and histological assessment," Rheumatology 38(5):401-406, 1999). Additional inhibitors of IL-1 signalling include recombinant soluble IL-1 receptors, and fusion proteins consisting of two IL-1 receptors attached to the Fc portion of a human IgG molecule (e.g., IL-1 trap, also known as RGN-303, is in clinical trials for RA); and monoclonal antibodies with a high affinity for IL-1 or IL-1R. Monoclonal antibodies with a high affinity for IL-1 will tend to reduce the biologic activity of IL-1; a number of potent IL-1R antagonist antibodies are known in the art, e.g., as described in Fredericks et al., "Identification of potent human anti-IL-1RI antagonist antibodies," Protein Eng. Des. Sel. 17(1):95-106, 2004). For additional inhibitors, see, e.g., U.S. Pat. No. 6,471,961 to Tobinick. Antibody based IL-1 blockers, such as anti-IL1a or anti-IL1b monoclonal antibodies can be generated using the human IL-1a protein sequence (accession no. CAG33695) or the human IL-1b protein sequence (accession no. CAG28607) using techniques known in the art.

In addition, IL-1 signalling inhibitors include inhibitory nucleic acids that decrease expression of IL-1 pathway molecules. Such inhibitory nucleic acids include antisense, small interfering RNAs, aptamers, ribozymes, and peptide-nucleic acids (PNAs) directed against a pathway molecule. For example, MyD88 antisense oligonucleotides are known in the art, see, e.g., U.S. Pat. No. 7,033,830 to Karras et al., and Vickers et al., "Modification of MyD88 mRNA splicing and inhibition of IL-1beta signaling in cell culture and in mice with a 2'-O-methoxyethyl-modified oligonucleotide," J. Immunol. 176(6):3652-61, 2006). IL-1 antisense oligonucleotides are known in the art, see, e.g., Watson et al., "The IL-1β-converting enzyme (caspase-1) inhibits apoptosis of inflammatory neutrophils through activation of IL-1β," J. Immunol., 161:957-62, 1998). IL-1R antisense oligonucleotides are known in the art, see, e.g., U.S. Pat. No. 5,856,099; and Burch and Mahan, "Oligonucleotides antisense to the interleukin 1 receptor mRNA block the effects of interleukin 1 in cultured murine and human fibroblasts and in mice," J. Clin. Invest. 88(4):1190-1196 (1991). Methods for identifying and using such inhibitory nucleic acids are well known, e.g., "gene walk" methods, and can be performed using, e.g., the human IL-1α sequence (accession no. BC013142) or the human IL-1β sequence (accession number BC008678). See, e.g., U.S. Pre-Grant Pub. No. 20060276458.

Furthermore, inhibitors of IL-1 signalling as used herein includes inhibitors of IL 1 production. For example, IL-1 is expressed as a non-functional pro molecule; cleavage by caspase produces the active form. Thus, IL-1 inhibitors include ICE/caspase inhibitors, a number of which are known in the art; see, e.g., Valentino et al., "First clinical trial of a novel caspase inhibitor: anti-apoptotic caspase inhibitor, IDN-6556, improves liver enzymes," Int. J. Clin. Pharmacol. Ther. 41(10):441-9, 2003) (describing IDN-6556, from Idun Pharmaceuticals, an anti-apoptotic agent); VX-740 (pralnacasan, Vertex Pharmaceuticals) and VX-765 (Vertex Pharmaceuticals) as anti-inflammatory agents; and z-VAD (R&D Systems). Pfizer has discovered three new classes of small molecule compounds that affect production, processing, or release of IL-1β, including cytokine-release inhibitory drugs (CRID), including diarylsulfonyl ureas such as CP-424174 and C-412245; IL-1β production inhibitors including pyridine-2 carboxylates such as CJ-14877 and CJ-14897; and a fungus-derived compound that also inhibits production of IL-1, LL-Z1271α. See, e.g., Randle et al., "ICE/Caspase-1 inhibitors as novel anti-inflammatory drugs," Exp. Op. Inv. Drugs, 10(7):1207-1209, 2001), and Braddock and Quinn, Nat. Rev. 3:1-10 (2004).

Screening Methods and Test Compounds

The invention includes methods for screening of test compounds, to identify compounds that inhibit IL-1 signalling, for use in a method of treatment or prophylaxis of sterile inflammation associated with cell necrosis as described herein. In some embodiments, the methods include first identifying test compounds that are capable of binding to IL-1 or a molecule in the IL-1 signalling pathway, and evaluating those test compounds that bind for the ability to inhibit IL-1 signalling activity. Such compounds can be useful in the prophylactic and therapeutic methods described herein.

Test Compounds

As used herein, a "test compound" can be any chemical compound, for example, a macromolecule (e.g., a polypeptide, a protein complex, glycoprotein, or a nucleic acid) or a small molecule (e.g., an amino acid, a nucleotide, an organic or inorganic compound, e.g., with a molecular weight of less than 1,000 Da), oligopeptides, oligonucleotides, or carbohydrates.

In some embodiments, the test compounds are initially members of a library, e.g., an inorganic or organic chemical library, peptide library, oligonucleotide library, or mixed-molecule library. In some embodiments, the methods include screening small molecules, e.g., natural products or members of a combinatorial chemistry library.

A given library can comprise a set of structurally related or unrelated test compounds. Preferably, a set of diverse molecules should be used to cover a variety of functions such as charge, aromaticity, hydrogen bonding, flexibility, size, length of side chain, hydrophobicity, and rigidity. Combinatorial techniques suitable for creating libraries are known in the art, e.g., methods for synthesizing libraries of small molecules, e.g., as exemplified by Obrecht and Villalgordo, Solid-Supported Combinatorial and Parallel Synthesis of Small-Molecular-Weight Compound Libraries, Pergamon-Elsevier Science Limited (1998). Such methods include the "split and pool" or "parallel" synthesis techniques, solid-phase and solution-phase techniques, and encoding techniques (see, for example, Czarnik, "Encoding methods for combinatorial chemistry," Curr. Opin. Chem. Bio. 1:60-6, 1997). In addition, a number of libraries, including small molecule libraries, are commercially available.

In some embodiments, the test compounds are peptide or peptidomimetic molecules, e.g., peptide analogs including peptides comprising non-naturally occurring amino acids or having non-peptide linkages; peptidomimetics (e.g., peptoid oligomers, e.g., peptoid amide or ester analogues, beta-peptides, D-peptides, L-peptides, oligourea or oligocarbamate); small peptides (e.g., pentapeptides, hexapeptides, heptapeptides, octapeptides, nonapeptides, decapeptides, or larger, e.g., 20-mers or more); cyclic peptides; other non-natural or unnatural peptide-like structures; and inorganic molecules (e.g., heterocyclic ring molecules). In some embodiments, the test compounds are nucleic acids, e.g., DNA or RNA oligonucleotides.

In some embodiments, test compounds and libraries thereof can be obtained by systematically altering the structure of a first test compound. Taking a small molecule as an example, e.g., a first compound is selected that has been identified as capable of binding to IL-1 or a molecule in the IL-1 signalling pathway. As one example, a general library of small molecules is screened, e.g., using a method described herein, to select a first test small molecule. Using methods known in the art, the structure of that small molecule is identified if necessary and correlated to a resulting biological activity, e.g., by a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds.

In some embodiments, test compounds identified as "hits" (e.g., test compounds that demonstrate the ability to bind to and inhibit signalling of IL-1) in a first screen are selected and optimized by being systematically altered, e.g., using rational design, to optimize binding affinity, avidity, specificity, or other parameter. Such potentially optimized structures can also be screened using the methods described herein. Thus, in one embodiment, the invention includes screening a first library of test compounds using a method described herein, identifying one or more hits in that library, subjecting those hits to systematic structural alteration to create one or more second generation compounds structurally related to the hit, and screening the second generation compound. Additional rounds of optimization can be used to identify a test compound with a desirable therapeutic profile.

Test compounds identified as hits, e.g., compounds that inhibit IL-1 signalling, can be considered candidate therapeutic compounds, useful in treating disorders described herein. In addition, a number of compounds are known in the art that inhibit IL-1 signalling, including those listed below. These compounds are also considered therapeutic compounds, and are useful in the methods described herein.

Screening Assays

As noted above, the screening assays can include, but are not limited to, one or both of a binding assay and a functional assay. Compounds that inhibit IL-1 signalling can be initially identified by the ability to bind to caspase, IL-1, IL-1R, MyD88, TRAF6, TAK1, NIK/MKK, IKK, or NF-kappaB.

Suitable binding assays are known in the art. For example, soluble compound libraries can be screened by affinity chromatography by contact with an immobilized molecule, e.g., IL-1, MyD88, or the IL-1 receptor, to isolate test compounds that bind to IL-1, MyD88, or the IL-1 receptor, followed by identification of the isolated test compound by conventional techniques (e.g., mass spectrometry, NMR, and the like). Immobilized test compounds can be screened by contacting the compounds with a soluble molecule, e.g., IL-1, MyD88, or IL-1 receptor (e.g., the soluble portion of the IL-1R); preferably, the soluble molecule is conjugated to a label (e.g., fluorophores, colorimetric enzymes, radioisotopes, luminescent compounds, and the like) that can be detected to indicate binding to an immobilized compound. Other suitable binding assays include, but are not limited to, Fluorescence Resonance Energy Transfer (FRET) assays, surface plasmon resonance (SPR) assays, radioligand binding assays, two-hybrid assays, and competitive binding assays (e.g., to identify compounds that compete with IL-1 for binding of the IL-1R, thereby inhibiting IL-1 signalling). Additional binding assays useful for screening test compounds are known in the art.

Functional assays are also known in the art that detect IL-1 signalling activity. For example, cytokine production assays can be used, e.g., IL-1 secretion assays, e.g., using immunohistochemistry, ELISA, or chip-based methods known in the art. As one example, a population of leukocytes can be contacted with injured or necrotic cells in the presence and absence of a test compound, and IL-1 secretion can be measured. A test compound that reduces IL-1 secretion in the presence of the injured or necrotic cells is a candidate inhibitor of IL-1 signalling. Alternatively or in addition, the activity of the IL-1 signalling pathway can be evaluated more directly using a cell containing a reporter gene linked to an IL-1 responsive promoter element, e.g., the interleukin response element (ILRE) in the IL-6 promoter, see, e.g., Shimizu et al., "Involvement of a NF-kappa B-like transcription factor in the activation of the interleukin-6 gene by inflammatory lymphokines," Mol. Cell. Biol. 10(2):561-8, 1990).

Pharmaceutical Compositions and Methods of Administration

The therapeutic compounds described herein (i.e., inhibitors of IL-1 signalling) can be incorporated into pharmaceutical compositions. Such compositions typically include the compound (i.e., as an active agent) and a pharmaceutically acceptable carrier. As used herein, "pharmaceutically acceptable carriers" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., anti-inflammatory compounds such as steroids, NSAIDS, cytokine neutralizing therapeutics such as anti-TNF therapeutics, and/or immunosuppressive agents such as cyclosporin or rapamycin.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

For administration by inhalation, the compounds are typically delivered in the form of an aerosol spray from pressured container or dispenser which contains a suitable propellant, e.g., a gas such as carbon dioxide, or a nebulizer. Such methods include those described in U.S. Pat. No. 6,468,798.

The therapeutic compounds can also be prepared in the form of suppositories (e.g., with conventional suppository bases such as cocoa butter and other glycerides) or retention enemas for rectal delivery.

Therapeutic compounds comprising nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., "Intranasal administration of HIV-DNA vaccine formulated with a polymer, carboxymethylcellulose, augments mucosal antibody production and cell-mediated immune response," Clin. Immunol. Immunopathol., 88(2):205-10, 1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Exemplary doses are as follows. For example, IL-1 R-FP when administered subcutaneously will generally be effective at a dosage level of between 10 mg and 250 mg (mean dose of 50 mg); when given intrathecally doses of between 0.5 mg and 25 mg (mean dose of 10 mg) will generally be used.

Monoclonal antibodies will generally be used at somewhat higher dosages, usually 0.5-25 mg/kg when administered peripherally, and 0.1-1.0 mg/kg when given intrathecally.

IL-1 RA and IL-1 R type II dosages will be similar and will approximate 0.02 to 3.0 mg/kg when given daily by subcutaneous bolus injection, and 0.01 to 0.5 mg/kg when administered intrathecally.

A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

The pharmaceutical compositions can be included in a container, pack, or dispenser together with instructions for administration.

EXAMPLES

The invention is further described in the following examples, which do not limit the scope of the invention described in the claims.

Methods

Animals and Cell Lines

C57BL/6, IL-1R−/−, and IL-18R−/− mice (8-12 weeks old) were purchased from The Jackson Laboratory. B6x129 F1 (B6129) mice (8-12 weeks old) were purchased from Taconic. MyD88−/− (Adachi et al., "Targeted disruption of the MyD88 gene results in loss of IL-1- and IL-18-mediated function," Immunity, 9:143-150, 1998), TIR Domain-Containing Adaptor Protein (TIRAP)/Mal−/− (Yamamoto et al., "Essential role for TIRAP in activation of the signalling cascade shared by TLR2 and TLR4," Nature, 420:324-329, 2002), TRIF−/− (Yamamoto et al, "Role of adaptor TRIF in the MyD88-independent toll-like receptor signaling pathway," Science, 301:640-643, 2003), TRAM−/− (Yamamoto et al, "TRAM is specifically involved in the Toll-like receptor 4-mediated MyD88-independent signaling pathway," Nat. Immunol., 4:1144-1150, 2003), TLR1−/− (Takeuchi et al., "Cutting edge: role of Toll-like receptor 1 in mediating immune response to microbial lipoproteins," J. Immunol., 169:10-14, 2002), TLR2−/− (Takeuchi et al., "Differential roles of TLR2 and TLR4 in recognition of gram-negative and gram-positive bacterial cell wall components," Immunity, 11:443-451, 1999), TLR3−/−, TLR4−/− (Hoshino, 1999), TLR6−/− (Takeuchi et al., "Discrimination of bacterial lipoproteins by Toll-like receptor 6," Int. Immunol., 13:933-940, 2001), TLR7−/− (Hemmi et al., Small anti-viral compounds activate immune cells via the TLR7 MyD88-dependent signaling pathway. Nat. Immunol., 3:196-200, 2002), and TLR9−/− (Hemmi et al., "A Toll-like receptor recognizes bacterial DNA," Nature, 408:740-745, 2000) mice were generated at the Department of Host Defense (Osaka University, Osaka, Japan). TLR11−/− (Zhang et al., "A toll-like receptor that prevents infection by uropathogenic bacteria," Science, 303:1522-1526, 2004) mice were kindly provided by Dr. Sanker Ghosh (Yale University). TLR2/4−/− mice were generated by crossing TLR2−/− with TLR4−/− mice. All animal studies have been approved by the Institute Animal Care and Use Committee, and all mice were kept in the University of Massachusetts Medical School animal facilities. EL4 and B 16 cells were maintained in hybridoma culture media (HCM) consisting of RPMI medium 1640 plus 10% FBS, 2 mM L-glutamine, 10 mM Hepes, penicillin/streptomycin, and 50 µM 2-mercaptoethanol. Hmgb1+/+ and Hmgb1−/− fibroblast cells were provided by Dr. Marco Bianchi (San Raffaele Scientific Institute, Italy) and maintained in DMEM plus 10% FBS.

Cell Injury Induction

EL4 cells were harvested by centrifugation, washed 3 times with PBS, and resuspended in PBS at a density of $13$-$20 \times 10^7$ cells/ml before subjected to heat shock at 45° C. for 10 minutes. Heat-shocked EL4 cells were incubated at 37° C. for 5 hours before challenged into animals. B16, Hmgb1+/+, and Hmgb1−/− cells cultured on 15-cm dishes were rinsed once with 10 ml of PBS and covered with 6 ml of PBS. The cells were then exposed to a UV source for 10 minutes, trypsinized, washed 3 times with PBS, and resuspended in PBS at a density of $13$-$20 \times 10^7$ cells/ml. UV-irradiated B16, Hmgb1+/+, and Hmgb1−/− cells were incubated at 37° C. for 5 hours before challenged into animals. Before challenged into animals, heat-shocked EL4 and UV-irradiated B16, Hmgb1+/+, and Hmgb1−/− cells were confirmed to be necrotic (Annexin V+, 7−AAD+). Mouse liver homogenate was prepared by first using a motor-driven potter homogenizer, and the homogenate was subject to five freeze-thaw cycles.

Acetaminophen (AAP) Treatment

Before experimental use, mice were fasted for 16-18 hours and were then injected i.p. with 300 mg/kg AAP or 20 ml/kg PBS. Eighteen hours after AAP administration, blood was drawn for serum collection and ALT assay (SYNCHRON LX Systems, Beckman Coulter), and mice were euthanized to obtain liver tissues for MPO activity assay.

Myeloperoxidase (MPO) Activity Assay

Mouse liver tissues were homogenized in MPO buffer (0.5% hexadecyl trimethyl ammonium bromide, 10 mM EDTA, 50 mM $Na_2HPO_4$, pH 5.4) using a Polytron homogenizer (Brinkmann). Liver homogenates were then subject to three freeze-thaw cycles and cleared by centrifugation to obtain the liver lysate. MPO reaction was carried out by first mixing 25 µl liver lysate with 25 µl assay buffer (1.67 mg/ml O-dianisidine, 50 mM $Na_2HPO_4$, pH 5.4) in a 96-well plate, and after adding 200 µl development solution (0.01% $H_2O_2$, 50 mM $Na_2HPO_4$, pH 5.4), absorbance at 450 nm was measured every 15 sec using the kinetic mode in a microplate reader.

Generation of Bone Marrow Chimeras

C57BL/6 and IL-1R−/− mice were lethally irradiated using 1100 rad. Bone marrow was prepared from the femurs and tibias of B6.SJL-Ptprca/BoAiTac (B6.SJL, CD45.1) or IL-1R−/− donor mice and depleted of T cells using a monoclonal antibody against Thy 1, M5/149 (ATCC) and complement (PEL-Freeze Biologicals). The irradiated mice were reconstituted intravenously (i.v.) with $2.5×10^6$ of different T cell-depleted bone marrow cells as indicated. The mice were then housed for 3-4 months to allow for the turnover and reconstitution of bone marrow-derived cells. The reconstitution of the chimeras was confirmed by staining blood leukocytes with anti-CD45.1 and anti-CD45.2 antibodies (BD Biosciences) and flow cytometric analysis.

Injured Cell-Induced Inflammation In Vivo

Mice were injected i.p. with $2-3×10^7$ necrotic EL4, B6, Hmgb1+/+, or Hmgb1−/− cells in 0.15 ml PBS, or 36 mg of mouse liver homogenate in 0.15 ml PBS. Equal volumes of PBS was injected into 2 mice and served as negative controls. At 16 hours after challenge, animals were euthanized by CO2 exposure, and their peritoneal cavities were washed with 7 ml of HCM containing 3 mM EDTA and 10 U/ml heparin. Total numbers of peritoneal exudate cells (PEC) were counted by a hematocytometer, and lavage fluids were centrifuged at 450×g for 10 minutes. Cells were resuspended in HCM and subjected to staining and flow cytometric analysis. Neutrophil and monocyte numbers in the PEC were determined by multiplying the total cell numbers with the percentage of Ly-6G+, 7/4+ cells and Ly-6G−, 7/4+ cells, respectively.

Flow Cytometric Analysis

PEC ($1×10^6$) were incubated with mAb 2.4G2 for 30 min to block FcγRIIB/III receptors, and stained with mAbs Ly-6G-FITC (BD Biosciences) and 7/4-biotin (Serotec) for 30 minutes at 4° C. The cells were further incubated with strepavidin-APC. Following staining, cells were washed with PBS, fixed in PBS containing 2% paraformaldehyde, and analyzed on a FACSCalibur (BD Biosciences) FACS analyzer. Data were acquired by CELLQUEST software and analyzed by FLOWJO software (Tree Star, Inc.).

Statistical Analyses

Statistical analysis in each independent experiment was performed with an unpaired, two-tailed Student's t-test. In FIGS. 2A-2J, data from multiple repeats were combined and analyzed using a linear mixed model (Fitzmaurice, 2004) with experiment as the random effect. Data are reported as mean±standard errors. $P<0.05$ was considered statistically significant.

Example 1

The Role of TIR Adaptor Proteins in Sterile Inflammation

In mammals TLR receptors play a major role in sensing the presence of microbes. When these receptors recognize microbial molecules they stimulate inflammation. It has been supposed that similar proteins and pathways are also activated during various types of sterile inflammation. However, it is presently unknown how important TLRs are in the inflammatory response provoked by dying cells.

TLRs signal through intracellular Toll/IL-1 receptor (TIR) adaptor molecules. The various TLRs utilize either one or several different TIR domain proteins: MyD88, TIRAP/Mal, TRIF, and TRAM. As a first step to examine whether TLRs are involved in mediating inflammation triggered by cell injury, the ability of mice deficient in each of the 4 TIR adaptors to respond to dead cells was analyzed. PBS or heat-shocked necrotic EL4 cells were injected intraperitoneally into wild type, MyD88$^{-/-}$, Mal$^{-/-}$, TRIF$^{-/-}$, or TRAM$^{-/-}$ mice. After 16 hours, the peritoneal cavities of the mice were lavaged and the cellular contents in the harvested fluid were quantified. The peritoneal cells (PEC) were stained with antibodies specific for Ly-6G and 7/4 and analyzed by flow cytometry. This allowed us to determine the number of neutrophils (Ly-6G$^+$7/4$^+$) and monocytes (Ly-6G$^-$7/4$^+$) recruited to the inflamed site. Neutrophil numbers in PEC were determined by multiplying the total cell numbers with the percentage of Ly-6G$^+$, 7/4$^+$ cells (n=3). The results, shown in FIG. 1A, indicated that mice injected with PBS had very few inflammatory cells present in the peritoneum, as expected. In contrast, necrotic EL4 cells induced strong infiltration of neutrophils and monocytes into the peritoneal cavity of wild type mice (FIG. 1A). Remarkably, neutrophil recruitment was dramatically impaired in MyD88$^{-/-}$ mice (FIG. 1B). Neutrophil recruitment in TRAM$^{-/-}$ mice was also significantly reduced, (FIG. 1C). There was no reduction in inflammation in mice deficient for TIRAP/Mal (FIG. 1D) and TRIF (FIG. 1D).

The strongly impaired neutrophil recruitment in MyD88$^{-/-}$ mice indicates that MyD88-mediated signaling plays a major role in the inflammatory response to injured cells. To exclude the possibility that MyD88 might be inherently unable to generate inflammation to any stimuli, mice were challenged with zymosan (yeast cell walls), and found that MyD88$^{-/-}$ mice generated a normal inflammatory response compared with the wild type mice (FIG. 1F). Therefore, the recruitment of inflammatory leukocytes to the site of inflammation is not inherently impaired in MyD88$^{-/-}$ mice, and MyD88 is specifically required during the sterile inflammation triggered by injured cells.

Example 2

The Role of TLRs in Sterile Inflammation to Injured Cells

The requirement of MyD88 and to a lesser extent TRAM during injured cell-induced inflammation suggested that TLRs could play a role in mediating this response. To investigate the role of TLRs in the sterile inflammatory response to dying cells, the response in mice that were genetically deficient in various TLRs was examined.

Necrotic EL4 cells were injected into the peritoneum of TLR-deficient mice and the acute inflammatory response was evaluated by quantifying the influx of neutrophils. The inflammation was modestly reduced in TLR2$^{-/-}$ and TLR4$^{-/-}$ mice, although this trend was not statistically significant in mice lacking only one or the other receptor (FIGS. 2B and 2D). In contrast, statistical analysis of the results of three independent experiments showed a significant reduction in neutrophil infiltration in TLR2/4 double-deficient animals compared with the wild type animals (FIG. 2I). These results indicate that TLR2 and TLR4 play some role in sensing/transducing inflammatory signals from injured cells. However, this role is not a dominant one since there is still a strong inflammatory response in the TLR2/4 double-deficient mice. The participation of TLR4 in the sterile inflammatory response is consistent with the findings that a TRAM-mediated pathway plays a minor role in the response to injured cells, since TLR4 signals through the TRAM TIR adaptor. In contrast, inflammation was not reduced in any of the other TLR-deficient mice (TLR1, 3, 6, 7, 9 and 11) (FIGS. 2A, C, E, F, G, and H). Therefore, there is no evidence that TLRs other than TLR2 and 4 are involved in the sterile inflammatory response. However, it is not known whether the two TLRs not tested (TLR5 and 8, for which mutant mice were not available) might be involved or whether multiple TLRs might be participating in a functionally redundant fashion.

Some of the TLR and adaptor mutant mice (TLR1, TLR3, TLR6, TLR7, TLR11, Mal, TRAM, and TRIF) were not fully backcrossed to the B6 background. Therefore, whether polymorphic 129 genes (the original strain of origin of the mutants) influence the inflammatory response in this system was evaluated. Conceivably polymorphic genes could affect the responsiveness of the host, or genetic differences between the host and injured cell might stimulate an alloreaction that might contribute to the inflammation. Since the inflammatory assay is of short duration and EL4 cells (of C57BL/6 origin) share the same MHC genes as 129 mice, it seemed highly unlikely that an alloreaction would contribute to the acute inflammatory response. Nevertheless, to rule out this possibility, necrotic EL4 cell-induced inflammation was compared in B6 and B6x129 F1 (B6129) mice. No significant differences in the inflammatory response between these two strains was found (FIG. 2J), indicating that after 129 mice are crossed to B6 background for one generation, the F1 hybrid mice and B6 mice exhibit similar inflammatory responses to necrotic EL4 cells. Since all mutant mice that were used in this study were backcrossed to B6 background for at least 3 generations, it is highly unlikely that genetic differences between B6129 hybrid mice and B6 mice confound the interpretation of data with the mutant animals not fully backcrossed onto the B6 background.

Example 3

Role of IL-1 and IL-18 Receptors in Sterile Inflammation to Injured Cells

The results from the experiments described thus far demonstrate that the inflammatory response to injured cells is much more dramatically affected by the loss of MyD88 than by the absence of any of the TLRs. These findings raised the possibility that a MyD88-dependent receptor other than TLRs might be involved in this process. There are in fact two other receptors that are known to utilize MyD88: the IL-1 receptor (IL-1R) and IL-18 receptor (IL-18R). Therefore, the ability of IL-1R and IL-18R-deficient mice to respond to injured cells was examined.

Necrotic EL4 cells were injected into the peritoneal cavity of IL-1R or IL-18R-deficient mice and the acute inflammatory response was evaluated. There was a reduction of 86.6% in the neutrophil response in IL-1R mutant mice at 16 hrs (FIG. 3A). In contrast the inflammatory response was not reduced in IL-18R-deficient mice (FIG. 3B). These results demonstrated that the IL-1R played an important role in neutrophil recruitment during the acute inflammatory response to injured cells. Since IL-1R signaling operates through MyD88, these results identify the IL-1R-MyD88 pathway as a major component of the neutrophilic sterile inflammatory response to injured cells. This almost certainly accounts for the much more dramatic phenotype observed in MyD88-deficient mice as compared to TLR null mice.

Example 4

IL-1R Functions on Non-Hematopoietic Cells in the Inflammatory Response to Injured Cells The IL-1R is broadly expressed and many cell types can produce IL-1. To further understand where the IL-1R-MyD88 pathway was needed to mount the inflammatory response, mice chimeric for the IL-1R were analyzed. Wild type mice that were reconstituted with IL-1R-deficient bone marrow (IL-1R$^{-/-}$→wt) showed no significant reduction in inflammatory responses to necrotic EL4 cells (FIG. 4A); therefore, the IL-1R is not required on leukocytes for this response. In contrast, IL-1R-deficient mice reconstituted with wild type bone marrow (wt→IL-1R$^{-/-}$) had markedly reduced inflammatory responses to injured EL4 cells (FIG. 4B). These results demonstrated that the IL-1R was required on radioresistant (non-bone marrow-derived), but not radiosensitive (bone marrow-derived) host cells, to respond to IL-1. In a separate set of chimeric mice whose bone marrow-derived but not other cells lacked MyD88, necrotic EL4 cell-stimulated neutrophil infiltration was at a similar level as in the control wild type chimeras (data not shown), indicating that MyD88 expression in bone marrow-derived cells is not essential for generating an inflammatory response to injured cells.

Example 5

The Inflammatory Response to Several Kinds of Injured Cells Requires MyD88 and IL-1R To determine whether the IL-1R and MyD88-signalling pathways were generally required for the inflammatory response to injured cells, their role in the sterile inflammatory response to additional types of dead cells was tested. B 16 melanoma cells (of C57BL/6 origin) were subject to UV irradiation injury, and the resulting necrotic B16 cells were injected into the peritoneal cavity of MyD88 or IL-1R-deficient mice. Subsequently, the acute inflammatory response was evaluated at 16 hours after challenge. Similar to necrotic EL4 cells, UV-irradiated B16 cells also induced strong influx of neutrophils and monocytes to the peritoneal cavity (FIG. 5B). In MyD88$^{-/-}$ mice, neutrophil recruitment was significantly reduced (FIG. 5B). A similar reduction in inflammatory leukocyte infiltration was also found in IL-1$^{-/-}$ mice; necrotic B16-induced neutrophil infiltration was strongly suppressed (FIG. 5B).

Both EL4 and B16 are transformed cell lines cultured in the laboratory for a long period of time, so the possibility of the presence of microbial components (e.g. viral genes/viral proteins) in these cells could not be ruled out. So in addition to the inflammation induced by dying cultured cells, the response triggered by necrotic primary cells was also examined. C57BL/6 mouse liver was homogenized mechanically and subjected to freeze-thaw cycles, and the resulting liver homogenate was injected into the peritoneal cavity of wild type, MyD88$^{-/-}$, or IL-1R$^{-/-}$ mice. Homogenized liver tissue induced as strong peritoneal inflammation as necrotic cultured cells (FIG. 6B); furthermore, the neutrophil influx was reduced in MyD88$^{-/-}$ mice (FIG. 6B) and IL-1R$^{-/-}$ mice (FIG. 6B). These experiments with cultured cells and primary tissues demonstrated that MyD88 and IL-1R play important regulatory roles in cell/tissue injury-induced inflammatory responses.

Example 6

Role of the IL-1R-MyD88 Pathway in the Monocyte Response in Sterile Inflammation Monocytes are also recruited to sites of cell injury. When the number of monocytes (Ly-6G$^-$7-4$^+$) recruited into the peritoneal cavity of MyD88-deficient mice injected with necrotic EL4, B16 or liver cells was analyzed, there was a modest reduction in recruitment of monocytes (FIG. 7A). Interestingly, the reduction in magnitude of this response was much less than was observed for neutrophils. A similar modest reduction in monocytes was observed when B16 and liver cells were injected into IL-1R-deficient mice (FIG. 7B). Surprisingly, for reasons that aren't clear the monocyte response to EL4 was actually significantly increased in the IL-1R null mice. These results indicate that during the acute inflammatory response triggered by injured cells, neutrophils and monocytes can be recruited to the inflamed site through somewhat different mechanisms. The recruitment of neutrophils is more dependent on IL-1 than for that of monocytes.

Example 7

Acetaminophen-Induced Liver Damage and Inflammation Requires IL-1R-Mediated Signaling All of the experiments described thus far have involved injecting dead cells into the peritoneum of mice. This example tested the generality of these findings to a situation where cell injury and death occurred in situ. For this purpose, an acetaminophen (AAP)-induced hepatotoxicity model was used where AAP-induced liver necrosis results in an inflammatory response (Jaeschke, "Mechanisms of Liver Injury. II. Mechanisms of neutrophil-induced liver cell injury during hepatic ischemia-reperfusion and other acute inflammatory conditions," Am. J. Physiol. Gastrointest. Liver Physiol., 290 (6):G1083-8, 2006; Jaeschke and Bajt, "Intracellular signaling mechanisms of acetaminophen-induced liver cell death," Toxicol. Sci., 89:31-41, 2006; Jaeschke, "Role of inflammation in the mechanism of acetaminophen-induced hepatotoxicity," Expert Opin. Drug Metab. Toxicol. 1(3):389-97, 2005).

To examine the role of IL-1R in AAP-induced liver injury and inflammation, an overdose of AAP (300 mg/kg) was administered intraperitoneally into mice, and serum alanine aminotransferase (ALT) activity and liver myeloperoxidase (MPO) activity were measured at 18 hours after challenge. ALT is a hepatocyte-specific enzyme and is released into blood during liver damage and hepatocyte necrosis; MPO is a neutrophil-specific enzyme and is used as a maker for neutrophil recruitment. The administration of AAP caused liver damage as indicated by the high serum ALT levels (FIG. 8A), and liver injury induced the recruitment of neutrophils to the liver tissue, which is thought to compound the tissue damage (FIG. 8B). Remarkably, both serum ALT and liver MPO activities were significantly reduced in IL-1R$^{-/-}$ mice, indicating that IL-1 is an important mediator for AAP-induced liver injury and neutrophilic inflammation.

Example 8

Role of HMGB1 in Sterile Inflammation

Since dead cells incite an inflammatory response, they must release or expose a proinflammatory molecule(s). To fully understand the pathways that generate the sterile inflammatory response, it will be important to understand this proinflammatory signal(s). It was reported that Hmgb1$^{-/-}$ necrotic cells had a reduced ability to promote inflammatory cytokine production by monocytes ex vivo, and antibodies to HMGB1 reduced inflammation to liver necrosis in vivo (Scaffidi, "Release of chromatin protein HMGB1 by necrotic cells triggers inflammation," Nature, 418:191-195, 2002), thus HMGB1 has been suggested to be a major proinflammatory factor released from damaged or necrotic cells. However, it is unknown whether HMGB1 is the only proinflammatory factor released from dead cells.

To investigate this issue, necrotic Hmgb1$^{-/-}$ fibroblasts were injected into the peritoneum of B6129 mice. As shown in FIG. 9A, mice also developed a strong acute inflammatory response to necrotic Hmgb1$^{-/-}$ fibroblasts, indicating that HMGB1 is not the only proinflammatory factor released from necrotic cells. When the inflammatory responses stimulated by necrotic Hmgb1$^{-/-}$ and Hmgb1$^{+/+}$ fibroblasts were compared, there was no significant difference in the influx of either neutrophils or monocytes (FIGS. 9A and B). Similar results were obtained when the HMGB1-positive and negative cells were injected subcutaneously and the neutrophil influx to the skin was determined by measuring the level of MPO at the injection site (data not shown). Therefore, HMGB1 is not the major proinflammatory factor that drives the inflammatory response to necrotic cells, at least in the case of fibroblasts.

REFERENCES

1. Kaisho and Akira, "Toll-like receptors as adjuvant receptors," Biochim. Biophys. Acta., 1589:1-13, 2002.
2. Kaisho and Akira, "Toll-like receptor function and signaling," J. Allergy Clin. Immunol., 117:979-987; quiz 988, 2006.
3. Akira and Takeda, "Toll-like receptor signaling," Nat. Rev. Immunol., 4:499-511. 2004.
4. Leadbetter et al., "Chromatin-IgG complexes activate B cells by dual engagement of IgM and Toll-like receptors," Nature, 416:603-607, 2002.
5. Means et al., "Human lupus autoantibody-DNA complexes activate DCs through cooperation of CD32 and TLR9," J. Clin. Invest., 115:407-417, 2005.
6. Lau et al., "RNA-associated autoantigens activate B cells by combined B cell antigen receptor/Toll-like receptor 7 engagement," J. Exp. Med. 202:1171-1177, 2005.
7. Barrat et al., "Nucleic acids of mammalian origin can act as endogenous ligands for Toll-like receptors and may promote systemic lupus erythematosus," J. Exp. Med., 202: 1131-1139, 2005.
8. Park et al., "Involvement of toll-like receptors 2 and 4 in cellular activation by high mobility group box 1 protein," J. Biol. Chem. 279:7370-7377, 2004.
9. Tsung et al., "The nuclear factor HMGB1 mediates hepatic injury after murine liver ischemia-reperfusion," J. Exp. Med. 201:1135-1143, 2005.
10. Park et al, "High mobility group box 1 protein interacts with multiple Toll-like receptors. Am J Physiol Cell Physiol 290:C917-924, 2006
11. Hoshino et al., "Cutting edge: Toll-like receptor 4 (TLR4)-deficient mice are hyporesponsive to lipopolysaccharide: evidence for TLR4 as the Lps gene product," J. Immunol., 162:3749-3752, 1999.
12. Fitzmaurice et al., *Applied Longitudinal Analysis*, John Wiley & Sons, Hoboken, United States, 2004.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating or delaying development or progression of sterile inflammation caused by necrosis in a subject, the method comprising administering to the subject a therapeutically effective amount of an antisense oligonucleotide or a small interfering RNA (siRNA) that specifically inhibits expression of Myeloid Differentiation Primary Response Gene 88 (MyD88).

2. The method of claim 1, further comprising:
   detecting the presence of necrotic cells or tissues in a subject who has, or is at risk of having sterile inflammation; and
   selecting the subject if necrotic cells are present.

3. The method of claim 1, wherein the sterile inflammation caused by necrosis is sterile inflammation associated with pancreatitis.

4. The method of claim 1, wherein the sterile inflammation caused by necrosis is sterile inflammation associated with ischemic injury.

5. The method of claim 4, wherein the ischemic injury is an injury to cardiac tissue, uterine tissue, renal tissue, hepatic tissue, neural tissue, muscle tissue, dermal tissue, or other organ.

6. The method of claim 4, wherein the ischemic injury is caused by a surgical intervention.

7. The method of claim 1, wherein the sterile inflammation caused by necrosis is caused by organ transplantation procedure.

8. The method of claim 7, wherein the necrosis is in the transplanted organ.

9. The method of claim 1, wherein the administration is local administration to the necrotic cells or a tissue or organ comprising the necrotic cells.

10. The method of claim 1, wherein the administration is local.

\* \* \* \* \*